United States Patent [19]
Van Dreden et al.

[11] Patent Number: 6,114,136
[45] Date of Patent: Sep. 5, 2000

[54] COMPOSITIONS USED AS A PATHOLOGICAL CONTROL IN A METHOD FOR THE DETECTION OF RESISTANCE TO ACTIVATED PROTEIN C, METHOD FOR THE PREPARATION OF THESE COMPOSITIONS AND USE IN SAID DETECTION METHOD

[75] Inventors: Patrick Van Dreden, Maisons-Alfort; Jean-Luc Martinoli, Villeneuve-la-Garenne, both of France

[73] Assignee: Diagnostica Stago, Asnieres, France

[21] Appl. No.: 09/316,005

[22] Filed: May 21, 1999

[30] Foreign Application Priority Data

May 22, 1998 [FR] France ................... 98 06464

[51] Int. Cl.$^7$ ............... C12Q 1/56; C12Q 1/00
[52] U.S. Cl. ............... 435/13; 435/4; 435/975; 435/967
[58] Field of Search ............... 435/13, 4, 975, 435/967

[56] References Cited

FOREIGN PATENT DOCUMENTS

| | | |
|---|---|---|
| 0 711 839 | 5/1996 | European Pat. Off. . |
| 0 761 686 | 3/1997 | European Pat. Off. . |
| 0 787 989 | 8/1997 | European Pat. Off. . |
| 91/01497 | 2/1991 | WIPO . |
| 94/17415 | 8/1994 | WIPO . |

OTHER PUBLICATIONS

Kraus et al.; "Factor V Leiden–Like Behaviour of Animal Plasma and its Use for Calibration of Activated Protein C–Dependent Assays"; Blood Coagulation and Fibrinolysis; vol. 7, No. 3; Apr. 1996; pp. 295–302; XP–002094489.

Le et al; "Blood" vol. 85(7); p. 1704–1711 (Abstract only), Apr. 1995.

Walker, F. J.; Thromb. Res. vol. 22(3); p. 321–317 (Abstract only), 1981.

*Primary Examiner*—Louise N. Leary
*Attorney, Agent, or Firm*—Foley & Lardner

[57] ABSTRACT

The invention relates to the use of a serum rich in factor Va for the preparation of compositions useful as pathological controls or calibrants in methods for analyzing resistance to activated protein C (APC), as well as said compositions, the method for their preparation and a method for the detection of resistance to activated protein C.

20 Claims, No Drawings

COMPOSITIONS USED AS A PATHOLOGICAL CONTROL IN A METHOD FOR THE DETECTION OF RESISTANCE TO ACTIVATED PROTEIN C, METHOD FOR THE PREPARATION OF THESE COMPOSITIONS AND USE IN SAID DETECTION METHOD

The invention relates to the use of a serum rich in factor Va for the preparation of compositions useful as pathological controls or calibrants in methods for analyzing resistance to activated protein C (APC), as well as said compositions, the method for their preparation and a method for the detection of resistance to activated protein C.

The study of hereditary thrombophilias has made it possible to demonstrate that resistance to APC (more commonly named according to the abbreviation APC-R) is mainly associated with mutations on the gene encoding factor V. The most widely known, called "Leiden mutation", "R506Q mutation" or "$^{506}R\rightarrow{}^{506}Q$ mutation" results, at the amino acid sequence of human factor V, in the replacement, at position 506, of an Arg residue to Gln, and predisposes to thrombosis, most often venous thrombosis. A large bibliography currently exists on the subject. Reference will be made in particular to the publications by Dahlbäck B. et al. (1993), Bertina R. M. et al. (1994), Kalafatis M. et al. (1994), De Ronde H. et al. (1994), Svensson P. J. et al. (1994) and Dahlbäck et al. (1994).

Other abnormalities in factor V may be responsible for APC-R. It is possible in particular that mutations at position 306 (that is to say $^{306}$Arg) of the amino acid sequence of factor V and/or factor Va (activated factor V) are one of the other possible causes of APC-R.

The first approaches to APC-R were carried out (in particular according to an APTT or KCCT test and the like) in order to assess the existence of a thrombotic risk factor by comparing the activated cephalin time, in the presence and in the absence of exogenous APC, for a control plasma with that for a sample to be tested. The addition of APC normally induces an extension of the clotting time. Indeed, PC in its activated form forms a complex with protein S and thus proceeds in particular to the proteolytic degradation of factor Va. This has the effect of slowing down the thrombotic activity of thrombin. As a result, clotting is delayed. In the event of an abnormality, this extension in the clotting time is more reduced than that observed in the healthy control (Mitchell C. A. et al. (1987), Amer L. et al. (1990) and Dahlbäck B. et al. (1991).

An assay kit is currently commercially available, marketed under the name "COATEST APC-RESISTANCE" by the company CHROMOGENIX (I.L.). This kit uses the method described in the publication by DAHLBÄCK et al. (1991) cited above and illustrated in WO-A-9310261 and the article by DAHLBÄCK et al. (1993), pages 1004–1008, cited above. This method comprises the mixing of one volume of plasma to be tested or of control plasma with one volume of APTT reagent (comprising phospholipids+an activator such as silica, kaolin or glass), incubation for 4 minutes at 37° C., and then the initiation of clotting by means of one volume of a solution of $CaCl_2$, on the one hand, or of the same volume of a solution of $CaCl_2$ supplemented with APC, on the other hand.

Several improvements or alternatives to this method have been described, especially in WO-A-9615457, WO-A-9604560 and EP-A-0711838.

In all the methods described, the response to APC is evaluated by comparing the clotting times obtained in the presence and in the absence of exogenous APC by conventional clotting methods (APTT, PT or RVVT Xa). Generally, the results are expressed in the form of two ratios $$APC\text{-}SR = \frac{\text{clotting time in the presence of } APC}{\text{clotting time in the absence of } APC}$$

$$nAPC\text{-}SR = \frac{APC\text{-}SR \text{ of the sample}}{APC\text{-}SR \text{ of the control plasma}}$$

However, the results obtained can vary considerably depending on the reagents and the measuring apparatus used and each laboratory has to define its own standards. As a result, the regions of normality and the cut-off values also exhibit heterogeneity. It is therefore important to be able to have standardized controls and/or calibrants in order to facilitate the interpretation of the results obtained, depending on the methods used.

In the case of clotting disorders linked to resistance to APC, the pathological controls or calibrants used should give results similar to those obtained from the plasma of sick patients, that is to say clotting times in the presence of APC which are below normal. However, since this reduction in the clotting time results from a mutation in factor V and not from a lack of functionality or from a nonfunctionality thereof, the conventional methods of preparing control plasmas (such as adsorption or dilution) from normal plasmas cannot be applied in order to produce plasmas reflecting this abnormality.

Given that the use of plasmas collected from patients is obviously inconceivable on an industrial scale, it has therefore proved necessary to find means of substitution.

A solution has thus been proposed in EP-0711839 which describes plasmas which can serve as calibrants in clotting tests evaluating the activity of the protein C/protein S system, or APC-R.

These plasmas are obtained by adding, to a normal human plasma, plasma obtained from animals, in particular citrated dog or preferably rabbit plasma. The addition of these animal plasmas produces a reduction in the clotting time, in an APC-dependent test, which is proportional to the quantity of non-human plasma added, thus making it possible to simulate a deficiency in the functional tests studying the activity of factor V and/or of the protein C/protein S system. EP-0711839 also indicates that the plasmas may be appropriate to a greater or lesser degree depending on the animal species studied, without, however, providing a precise explanation for this observation.

The use of animal plasmas, as recommended in this application, therefore offers the possibility of easily obtaining controls simplifying the evaluation of the results obtained from various tests. However, it may have some disadvantages depending on the conditions for the clotting tests performed.

Thus, the simulation of an APC-R requires the addition of at least 5% plasma in the case of rabbits, or even two to three times more in the case of another animal. This addition to the normal human plasma may create a dilution effect which may interfere with the interpretation of the results. Moreover, the animal plasmas used contain high levels of factors II and VII, known to be factors of instability (LEWIS J. H., 1996). Problems can therefore occur during the preservation of this type of reagent. Moreover, problems of supply may also arise for the recommended plasmas, linked, for example, to the difficulties of collecting samples and the small volume of animal blood (in the case of rabbits for example).

The authors of the present invention have tried to develop compositions representative of a plasma containing a Leiden factor V and more precisely a plasma having a clotting time in the presence of APC situated in the interval defined for an APC-R plasma. The aim of this approach is to have available plasmas simulating the behavior of APC-R plasmas and to use them as pathological controls when the plasma to be tested is an APC-R plasma or is strongly suspected of being one.

Two approaches are theoretically possible for the production of such an "APC-R-like" plasma.

The first consists in inducing inhibition of APC with the aid of specific compounds, thus creating a situation in which factor Va is no longer inhibited.

The second approach consists in inducing a saturation of APC, that is to say a situation in which factor Va is found to be present in quantities such that APC is only capable of cleaving a portion thereof. The excess of factor Va remaining active may then induce a clotting time identical to that of an APC-R plasma.

The authors of the present invention adopted the second approach. They therefore tried to select a nonhuman source of factor Va which can be added to a normal plasma so as to simulate an APC-R plasma, without this inducing an excessively high dilution or instability of this plasma, or interference linked to the concomitant supply of other factors.

The authors of the present invention were able to observe that the addition of very small quantities of animal, in particular bovine, serum rich in factor Va to normal human plasma induced a reduction in the clotting time in the presence of APC. They thus obtained pathological control plasmas by selecting, from ranges of dilution of animal serum rich in factor Va in normal human plasmas, the samples having a clotting time situated in the interval for that of an APC-R plasma. Moreover, given that the reduction in the clotting time for the plasma depends on the quantity of added serum up to complete inhibition of the action of APC (cut-off corresponding to the minimum clotting time), the studies by the inventors also make it possible to prepare compositions which can be used as calibrants for this type of test.

In addition to the advantages stated above (low dilution of the plasma, negligible supply of other clotting factors and of factors interfering with the reactions), the use of animal sera rich in factor Va has another benefit in terms of specificity. It has indeed been shown that factor V increased the proteolytic degradation of factor VIII by APC, even in the absence of protein S, whereas factor Va did not have this cofactor action (VARADI K. et al., 1995). However, factor V exists in its activated form in serum, whereas it is in its nonactivated form in the plasma. The addition of a serum therefore offers, compared with that of a plasma, greater specificity for the action of APC on factor Va and is thus particularly advantageous for tests for detecting APC-R.

The subject of the present invention is therefore the use of an animal serum rich in factor Va for the production of compositions useful as pathological controls or calibrants in a method for the detection of resistance to activated protein C.

It also relates to compositions useful as pathological controls or calibrants for a method for the detection of resistance to APC comprising animal serum rich in factor Va and normal plasma.

The subject of the invention is, in addition, a method for the preparation of compositions useful as pathological controls or calibrants in a method for the detection of resistance to APC comprising normal plasma enriched with nonhuman factor Va.

"Normal plasma" is understood to mean a normal plasma or a pool of normal plasmas.

The invention finally comprises a method for the detection of resistance to APC and the kits for using them comprising, as pathological control or calibrant, a composition as defined above.

According to a first aspect, the subject of the present invention is the use of an animal serum rich in factor Va for the applications targeted above.

The serum may be obtained from various animal species. Thus, within the context of the present invention, "animal serum" is understood to mean an animal serum or a pool of animal sera from various species or otherwise. The serum is preferably of bovine origin.

Indeed, compared with human plasma considered as containing 100% factor V, 500% of this factor is measured in the plasma, and up to 2000 to 3500% of factor V in its activated form (factor Va) is measured in the serum in bovines (these quantities are expressed relative to a reference consisting of a pool of human plasmas from healthy donors, in which the factor V level is supposed to be 100% or 1 U/ml, Karges H. E. et al., (1994)).

A serum with a high factor Va concentration may thus be used in much smaller quantities than those necessary for plasmas, which makes it possible to avoid problems of dilution of the normal plasma in the compositions according to the invention.

Preferably, a pool of serum containing more than 2000% of factor Va, and more preferably more than 2200%, is used.

Such quantities of factor Va in the serum make it possible to use it in final dilution ranges of between 1/300 and 1/1200, and preferably between 1/400 and 1/1000.

Advantageously, the animal serum used is treated so as to eliminate or avoid the effects of factors which may be responsible for instability or interference. These factors are in particular vitamin K-dependent factors such as factors II, VII, IX and X, protein S, protein C and protein Z. Traces of fibrin are also eliminated.

These factors may be eliminated by carrying out adsorption of the serum on barium sulfate, as described by SOULIER J. P., (1975).

According to another aspect, the present invention relates to compositions useful as pathological controls or calibrants in a method for the detection of resistance to APC, comprising normal serum and animal serum rich in factor Va. Preferably, the normal plasma is human plasma, and more preferably citrated human plasma.

In an advantageous variant, said compositions comprise bovine serum, containing more than 2000% of factor Va and preferably more than 2200%. The serum is present in the compositions at dilutions ranging from 1/300 to 1/1200 and preferably from 1/400 to 1/1000.

The pool of serum is preferably treated as described above, by adsorption on barium sulfate and bentonite, or another absorbent.

The compositions according to the invention may be advantageously provided in lyophilized form.

The present invention also comprises a method for the preparation of said compositions. These consist in carrying out a range of dilutions of a pool of animal serum rich in factor Va, preferably bovine serum containing more than 2000% of factor Va, and more preferably more than 2200%, in a normal plasma or a pool of normal, preferably human, plasmas and in selecting the samples for which the clotting time in the presence of APC is situated in the interval defined for the clotting time in the presence of APC of an APC-R plasma. A detailed protocol for the preparation of the compositions according to the invention is described below.

1. Raw materials:
   Human plasma
   Hydrochloric acid R.P.
   Sodium hydroxide R.P.
   Frozen adsorbed bovine serum
2. Production:
2.1 Preparation of the serum
   The serum is prepared from bovine plasma clotted with a mixture of thrombin, phospholipids, $Ca^{2+}$,
   the bovine serum frozen and adsorbed beforehand at 37° C. for 30 minutes on 10% barium sulfate w/v (twice) is thawed,
   the serum is adsorbed on bentonite (5‰) for 20 minutes, and
   the supernatant obtained after centrifugation is filtered.
2.2. Selection of the compositions:
   a range of dilutions of the serum is prepared in a pool of normal human plasma in order to obtain final serum dilutions of between 1/300 and 1/1200,
   stirring is carried out for 5 minutes at room temperature,
   the samples prepared are tested according to the "STA-Staclot APC-R" method as described in "A New Chronometric Assay based on the Va Dependent procoagulant activity of a snake venom for the detection of Factor V Leiden", XVIth Congress of the ISTH—Florence (Italy), Jun. 6–12, 1997 or in "Automated detection of the Factor V Leiden using a new screening test: STA Staclot-APC-R", 15th International Congress on Thrombosis-Antalya (Turkey) Oct. 15–21, 1998, relative to a pool of references (on STA),
   the sample for which the clotting time in the presence of APC is between 60 and 90 seconds, corresponding to the normalized ratio for an APC-R plasma of between 0.40 and 0.65 is selected.
2.3. Standard lyophilization is carried out for 48 hours The use of the compositions according to the invention in a method for the detection of resistance to APC makes it possible to check the quality of the assay carried out.

The subject of the invention is therefore also a method for the detection of resistance to APC in a plasma to be tested which consists in comparing the clotting time measured for said plasma with the clotting time measured for control compositions in accordance with the invention each having different dilutions of the animal serum rich in factor Va. The clotting time measured for the composition in accordance with the invention which is closest, or even identical, to that measured for the plasma to be tested will be indicative of the level of resistance to APC of said plasma because the quantity of factor Va added to said control composition is exactly known.

The clotting method used may be chronometric or chromogenic. It is preferably a chronometric method based on the measurement of the clotting time for the sample to be studied, supplemented with a plasma deficient in factor V, with a venom (factor V dependent) and with $CaCl_2$ with or without APC. The results may be expressed in the form of a normalized ratio, or preferably as time or OD.

The compositions of the invention may therefore advantageously enter into the constitution of a kit for the diagnosis of resistance to activated protein C, as a pathological control. They may be preferably provided in lyophilized form for their preservation, and will be reconstituted at the time of use with distilled water.

The subject of the present invention is also such a diagnostic kit.

The invention will be understood more clearly in the light of the examples below which are given solely by way of illustration.

EXAMPLES

In all the tables below, "−APC" means that no APC was added to the test, "+APC" means that exogenous APC was added to the test.

Example 1

Preparation of a Calibrant

The determination of the clotting time is carried out on an automated STA® machine by a chronometric assay according to the STA-STACLOT®-APC®-R method cited above.

The normal human plasma is citrated plasma obtained from a pool of 30 normal plasmas.

The pool of animal serum used is bovine serum containing more than 2200% of factor Va.

The clotting times as a function of the dilution of the serum in the plasma are presented in Table I below.

The clotting times (expressed in seconds) decrease with the final dilutions of the serum in the plasma.

The use of a serum according to the invention therefore makes it possible to obtain compositions useful as calibrants.

TABLE I

| Final dilution of the serum | 1/100 | 1/200 | 1/300 | 1/400 | 1/500 | 1/700 | 1/1000 | 0 |
|---|---|---|---|---|---|---|---|---|
| Clotting time | 24.5 | 38.8 | 47.8 | 52.7 | 57.3 | 61.2 | 77.4 | 180 |

Example 2

Comparison of the Results Obtained With the "Coatest APC-Resistance" Method (CHROMOGENIX) and the STA-STACLOT® APC-R Method.

The results obtained with an example of a composition according to the invention which is used as a pathological control in the "COATEST APC-resistance" method and in the STA-STACLOT®-APC®-R method cited above, are presented in Table II Table II indicates that the compositions of the invention may be advantageously used in a test for the detection of resistance to APC.

TABLE II

| | Composition according to the invention | | | Pool of normal human plasmas | | |
|---|---|---|---|---|---|---|
| | Clotting time | | Standard ratio | Clotting time | | Standard ratio |
| | −APC | +APC | (APC-SR) | −PC | +APC | (APC-SR) |
| COATEST method | 39.6 | 61.3 | 1.54 | 57.8 | 218.9 | 3.78 |
| STA-STACLOT APC-R method | 38.5 | 67.2 | 1.74 | 50.7 | 177.8 | 3.51 |

Example 3

Intra-Assay Reproducibility

In order to estimate the intra-assay reproducibility of the Pathological Controls on STA, 21 determinations were carried out, starting with three pathological control compositions, with the same reagent kit, STA® STA-CLOT® APC-R. The results relating to the coefficient of variation (CV) are given in Table III below. They indicate that the CV of the normalized ratio nSR-APC-R or of the time in the presence of APC is less than 5%.

TABLE III

| | CRT P: 7349A1D | | | | CRT P: 8005AD | | | | CRT P: 8005B3D | | | |
|---|---|---|---|---|---|---|---|---|---|---|---|---|
| | −APC | +APC | APC-SR | n-APC-SR | −APC | +APC | APC-SR | n-APC-SR | −APC | +APC | APC-SR | n-APC-SR |
| Pool 08/97 | 37.2 | 158.4 | 4.26 | | | | | | | | | |
| | 40.3 | 155.0 | 3.87 | | | | | | | | | |
| 1 | 40.1 | 80.9 | 2.02 | 0.50 | 37.5 | 67.8 | 1.81 | 0.44 | 38.4 | 68.4 | 1.78 | 0.44 |
| 2 | 40.8 | 80.4 | 1.97 | 0.48 | 38.6 | 67.6 | 1.75 | 0.43 | 39.0 | 70.8 | 1.82 | 0.45 |
| 3 | 40.2 | 78.5 | 1.95 | 0.48 | 39.0 | 67.4 | 1.73 | 0.43 | 39.4 | 69.9 | 1.77 | 0.44 |
| 4 | 41.7 | 79.5 | 1.91 | 0.47 | 38.0 | 70.1 | 1.84 | 0.45 | 39.2 | 69.7 | 1.78 | 0.44 |
| 5 | 40.4 | 82.3 | 2.04 | 0.50 | 39.0 | 68.6 | 1.76 | 0.43 | 39.5 | 68.3 | 1.73 | 0.43 |
| 6 | 40.2 | 79.7 | 1.98 | 0.49 | 38.4 | 67.2 | 1.75 | 0.43 | 38.6 | 69.2 | 1.79 | 0.44 |
| 7 | 40.4 | 78.4 | 1.94 | 0.48 | 38.4 | 67.7 | 1.76 | 0.43 | 38.9 | 68.9 | 1.77 | 0.44 |
| 8 | 39.5 | 77.4 | 1.96 | 0.48 | 38.5 | 67.8 | 1.76 | 0.43 | 38.8 | 71.0 | 1.83 | 0.45 |
| 9 | 40.1 | 80.0 | 2.00 | 0.49 | 38.3 | 69.1 | 1.80 | 0.44 | 38.4 | 69.6 | 1.81 | 0.45 |
| 10 | 40.8 | 78.3 | 1.92 | 0.47 | 38.6 | 68.2 | 1.77 | 0.43 | 38.6 | 70.1 | 1.82 | 0.45 |
| 11 | 41.3 | 80.7 | 1.95 | 0.48 | 38.7 | 67.7 | 1.75 | 0.43 | 38.6 | 69.7 | 1.81 | 0.44 |
| 12 | 40.5 | 79.1 | 1.95 | 0.48 | 38.3 | 68.0 | 1.78 | 0.44 | 39.0 | 68.3 | 1.75 | 0.43 |
| 13 | 40.0 | 79.0 | 1.98 | 0.49 | 38.6 | 68.1 | 1.76 | 0.43 | 39.1 | 69.9 | 1.79 | 0.44 |
| 14 | 40.6 | 80.3 | 1.98 | 0.49 | 38.6 | 68.2 | 1.77 | 0.43 | 39.1 | 68.3 | 1.75 | 0.43 |
| 15 | 41.0 | 77.6 | 1.89 | 0.47 | 39.0 | 69.5 | 1.78 | 0.44 | 39.3 | 68.7 | 1.75 | 0.43 |
| 16 | 40.3 | 78.7 | 1.95 | 0.48 | 38.2 | 67.9 | 1.78 | 0.44 | 38.9 | 67.8 | 1.74 | 0.43 |
| 17 | 41.2 | 80.8 | 1.96 | 0.48 | 38.8 | 69.o | 1.78 | 0.44 | 39.6 | 69.1 | 1.74 | 0.43 |
| 18 | 39.8 | 78.0 | 1.96 | 0.48 | 38.9 | 69.0 | 1.77 | 0.44 | 38.9 | 68.6 | 1.76 | 0.43 |
| 19 | 40.0 | 80.8 | 2.02 | 0.50 | 38.7 | 68.4 | 1.77 | 0.43 | 39.0 | 67.8 | 1.74 | 0.43 |
| 20 | 41.3 | 80.2 | 1.94 | 0.48 | 38.1 | 69.2 | 1.82 | 0.45 | 38.6 | 69.2 | 1.79 | 0.44 |
| 21 | 40.7 | 79.3 | 1.95 | 0.48 | 38.8 | 68.0 | 1.75 | 0.43 | 38.8 | 68.2 | 1.76 | 0.43 |
| MEAN | 40.52 | 79.52 | 1.96 | 0.48 | 38.52 | 68.31 | 1.77 | 0.44 | 38.94 | 69.12 | 1.78 | 0.44 |
| SD | 0.56 | 1.26 | 0.04 | 0.01 | 0.37 | 0.75 | 0.03 | 0.01 | 0.34 | 0.92 | 0.03 | 0.01 |
| CV | 1.38 | 1.59 | 1.81 | 1.81 | 0.97 | 1.10 | 1.49 | 1.49 | 0.87 | 1.33 | 1.66 | 1.66 |

Example 4

Reproducibility Per Batch

Three batches of pathological control compositions were tested here on STA with the same batch of reagents (STA® STACLOT® APC-R: 010). Each plasma is tested twice in the same series (on 1 bottle). Fifteen independent series (15 bottles of the same batch) were performed.

Table IV below shows that the coefficient of variation (CV) of the times with APC is less than 5%.

TABLE IV

| Bottles | CRT P: 7349A1D | | | | CRT P: 8005A2D | | | |
|---|---|---|---|---|---|---|---|---|
| | −APC | +APC | APC-SR | n-APC-SR | APC | +APC | APC-SR | n-APC-gR |
| 1 | 42.2 | 83.2 | 1.97 | 0.48 | 39.0 | 68.7 | 1.76 | 0.43 |
| | 42.2 | 83.4 | 1.98 | 0.48 | 39.1 | 70.1 | 1.79 | 0.44 |
| 2 | 41.9 | 83.6 | 2.00 | 0..49 | 39.0 | 68.7 | 1.76 | 0.43 |
| | 42.5 | 82.0 | 1.93 | 0.47 | 39.3 | 68.5 | 1.74 | 0.43 |
| 3 | 41.3 | 82.2 | 1.99 | 0.49 | 39.0 | 68.3 | 1.75 | 0.43 |
| | 42.2 | 81.4 | 1.93 | 0.47 | 39.2 | 68.1 | 1.74 | 0.42 |
| 4 | 42.0 | 83.3 | 1.98 | 0.48 | 40.0 | 68.5 | 1.71 | 0.42 |
| | 41.6 | 82.4 | 1.98 | 0.48 | 39.7 | 68.7 | 1.73 | 0.42 |
| 5 | 42.1 | 81.8 | 1.94 | 0.47 | 39.0 | 68.3 | 1.7.5 | 0.43 |
| | 41.8 | 79.8 | 1.91 | 0.47 | 39.2 | 69.6 | 1.78 | 0.43 |
| 6 | 42.2 | 82.4 | 1.95 | 0.48 | 39.3 | 67.7 | 1.72 | 0.42 |
| | 41.7 | 81.8 | 1.96 | 0.48 | 39.0 | 69.8 | 1.79 | 0.44 |
| 7 | 41.1 | 80.7 | 1.96 | 0.48 | 39.0 | 68.2 | 1.75 | 0.43 |
| | A1.4 | 80.1 | 1.93 | 0.47 | 39.0 | 68.6 | 1.76 | 0.43 |
| 8 | 41.8 | 82.0 | 1.96 | 0.48 | 38.4 | 68.5 | 1.78 | 0.44 |

TABLE IV-continued

|    | | | | | | | | |
|----|------|------|------|------|------|------|------|------|
|    | 41.5 | 81.2 | 1.96 | 0.48 | 39.0 | 68.4 | 1.75 | 0.43 |
| 9  | 41.3 | 81.1 | 1.96 | 0.48 | 39.8 | 67.9 | 1.71 | 0.42 |
|    | 41.4 | 80.9 | 1.95 | 0.48 | 40.1 | 70.1 | 1.75 | 0.43 |
| 10 | 40.6 | 80.6 | 1.99 | 0.48 | 39.2 | 67.9 | 1.73 | 0.42 |
|    | 41.3 | 81.9 | 1.98 | 0.48 | 39.1 | 67.7 | 1.73 | 0.42 |
| 11 | 40.6 | 78.9 | 1.94 | 0.47 | 39.4 | 69.1 | 1.75 | 0.43 |
|    | 41.1 | 82.6 | 2.01 | 0.49 | 40.1 | 67.8 | 1.69 | 0.4i |
| 12 | 40.0 | 79.6 | 1.99 | 0.49 | 40.4 | 67.9 | 1.68 | 0.41 |
|    | 41.0 | 79.0 | 1.93 | 0.47 | 40.2 | 68.4 | 1.70 | 0.42 |
| 13 | 39.4 | 81.0 | 2.06 | 0.50 | 39.4 | 68.9 | 1.75 | 0.43 |
|    | 39.9 | 82.0 | 2.06 | 0.50 | 39.9 | 67.1 | 1.68 | 0.41 |
| 14 | 39.3 | 81.2 | 2.07 | 0.50 | 39.3 | 68.9 | 1.75 | 0.43 |
|    | 39.4 | 79.9 | 2.03 | 0.50 | 39.4 | 68.4 | 1.74 | 0.42 |
| 15 | 38.7 | 81.6 | 2.11 | 0.51 | 38.7 | 68.1 | 1.76 | 0.43 |
|    | 38.7 | 81.4 | 2.10 | 0.51 | 38.7 | 68.9 | 1.78 | 0.43 |
| MEAN | 41.1 | 81.4 | 1.98 | 0.48 | 39.3 | 68.5 | 1.74 | 0.43 |
| SD | 1.02 | 1.27 | 0.05 | 0.01 | 0.48 | 0.71 | 0.03 | 0.01 |
| CV | 2.48 | 1.55 | 2.33 | 2.33 | 1.23 | 1.04 | 1.69 | 1.69 |

| | CRT P: 8005B3D | | | |
|---|---|---|---|---|
| Bottles | −APC | +APC | APC-SR | n-APC-SR |
| 1  | 39.2 | 69.4 | 1.77 | 0.43 |
|    | 40.0 | 69.0 | 1.73 | 0.42 |
| 2  | 39.4 | 69.6 | 1.77 | 0.43 |
|    | 39.6 | 68.9 | 1.74 | 0.42 |
| 3  | 40.2 | 68.5 | 1.70 | 0.42 |
|    | 39.5 | 68.5 | 1.73 | 0.42 |
| 4  | 39.7 | 69.8 | 1.76 | 0.43 |
|    | 39.7 | 70.0 | 1.76 | 0.43 |
| 5  | 39.5 | 72.8 | 1.84 | 0.45 |
|    | 39.8 | 69.7 | 1.75 | 0.43 |
| 6  | 40.7 | 69.8 | 1.71 | 0.42 |
|    | 39.8 | 71.0 | 1.78 | 0.44 |
| 7  | 39.3 | 69.9 | 1.78 | 0.43 |
|    | 39.3 | 69.0 | 1.76 | 0.43 |
| 8  | 39.4 | 68.6 | 1.74 | 0.43 |
|    | 39.5 | 68.8 | 1.74 | 0.43 |
| 9  | 39.3 | 68.2 | 1.74 | 0.42 |
|    | 39.3 | 67.9 | 1.73 | 0.42 |
| 10 | 39.4 | 68.6 | 1.74 | 0.43 |
|    | 39.2 | 69.2 | 1.77 | 0.43 |
| 11 | 39.2 | 69.5 | 1.77 | 0.43 |
|    | 39.7 | 68.0 | 1.71 | 0.42 |
| 12 | 39.3 | 67.5 | 1.72 | 0.42 |
|    | 40.2 | 68.4 | 1.70 | 0.42 |
| 13 | 39.7 | 66.4 | 1.67 | 0.41 |
|    | 40.1 | 64.6 | 1.61 | 0.39 |
| 14 | 39.6 | 67.0 | 1.69 | 0.41 |
|    | 39.4 | 66.5 | 1.69 | 0.41 |
| 15 | 39.0 | 65.7 | 1.68 | 0.41 |
|    | 39.7 | 67.0 | 1.69 | 0.41 |
| MEAN | 39.6 | 68.6 | 1.73 | 0.42 |
| SD | 0.37 | 1.61 | 0.04 | 0.01 |
| CV | 0.95 | 2.35 | 2.49 | 2.49 |

Example 5

Day-To-Day Reproducibility

With the aim of estimating the day-to-day reproducibility, the same batch of Pathological Control was tested over 10 days with the same batch of reagents (STA® Staclot® APC-R 010) on the same STA. The normalized ratios are derived from a daily assay of the aliquoted pool.

Table V below shows that the CV of the ratios or of the times in the presence of APC on a day-to-day is less than 5%.

TABLE V

| | CRT P: 7349A1D | | | | CRT P: 8005A2D | | | | CRT P: 8005B3D | | | |
|---|---|---|---|---|---|---|---|---|---|---|---|---|
| Days | −APC | +APC | APC-SR | n-APC-SR | −APC | +APC | APC-SR | n-APC-SR | −APC | +APC | APC-SR | n-APC-SR |
| Pool 08/97 | 40.1 | 162.4 | 4.05 | | | | | | | | | |

TABLE V-continued

| | CRT P: 7349A1D | | | | CRT P: 8005A2D | | | | CRT P: 8005B3D | | | |
|---|---|---|---|---|---|---|---|---|---|---|---|---|
| Days | −APC | +APC | APC-SR | n-APC-SR | −APC | +APC | APC-SR | n-APC-SR | −APC | +APC | APC-SR | n-APC-SR |
| 1 | 40.9 | 78.9 | 1.93 | 0.48 | 39.1 | 68.0 | 1.74 | 0.43 | 39.7 | 69.9 | 1.76 | 0.43 |
| 2 | 40.8 | 78.4 | 1.92 | 0.47 | 39.7 | 69.4 | 1.75 | 0.43 | 39.5 | 69.2 | 1.75 | 0.43 |
| 3 | 41.8 | 77.9 | 1.86 | 0.46 | 39.3 | 66.3 | 1.69 | 0.42 | 39.7 | 67.4 | 1.70 | 0.42 |
| 4 | 41.9 | 78.5 | 1.87 | 0.46 | 39.3 | 65.8 | 1.67 | 0.41 | 39.6 | 68.7 | 1.73 | 0.43 |
| 5 | 41.7 | 83.2 | 2.00 | 0.49 | 39.0 | 68.4 | 1.75 | 0.43 | 39.7 | 70.5 | 1.78 | 0.44 |
| 6 | 42.2 | 82.4 | 1.95 | 0.48 | 38.8 | 67.8 | 1.75 | 0.43 | 39.6 | 69.4 | 1.75 | 0.43 |
| 7 | 40.7 | 84.5 | 2.08 | 0.51 | 39.4 | 70.2 | 1.78 | 0.44 | 40.3 | 72.3 | 1.79 | 0.44 |
| 8 | 42.2 | 84.9 | 2.01 | 0.50 | 39.6 | 69.3 | 1.75 | 0.43 | 40.2 | 72.2 | 1.80 | 0.44 |
| 9 | 40.8 | 81.1 | 1.99 | 0.49 | 38.6 | 69.5 | 1.8 | 0.44 | 38.9 | 68.9 | 1.77 | 0.44 |
| 10 | 41.5 | 80.6 | 1.94 | 0.48 | 39.1 | 69.6 | 1.78 | 0.44 | 38.9 | 68.3 | 1.76 | 0.43 |
| MEAN | 41.45 | 81.04 | 1.96 | 0.48 | 39.19 | 68.43 | 1.75 | 0.43 | 39.61 | 69.68 | 1.76 | 0.43 |
| SD | 0.6 | 2.61 | 0.06 | 0.02 | 0.34 | 1.47 | 0.04 | 0.01 | 0.46 | 1.60 | 0.03 | 0.01 |
| CV | 1.44 | 3.22 | 3.30 | 3.30 | 0.87 | 2.14 | 2.27 | 2.27 | 1.15 | 2.29 | 1.64 | 1.64 |

Example 6

Batch-To-Batch Overlapping

Three Pathological Controls are determined on the same batch of reagents (STA® Staclot® APC-R 010). Each sample was subject to 5 measurements. The same pool was also assayed in parallel in order to determine the nSR-APC-R.

Table VI below indicates that there is good overlapping of the batches, the target value being 0.40–0.55 for a pathological control.

TABLE VI

| | CRT P: 7349A1D | | | | CRT P: 8005A2D | | | | CRT P: 8005B3D | | | |
|---|---|---|---|---|---|---|---|---|---|---|---|---|
| | −APC | +APC | APC-SR | C-APC-SR | −APC | +APC | APC-SR | n-APC-SR | −APC | +APC | APC-SR | n-APC-SR |
| Pool 08/97 | 36.7 | 161.7 | 4.41 | | | | | | | | | |
| | 39.4 | 163.8 | 4.16 | | | | | | | | | |
| 1 | 41.3 | 85.8 | 2.08 | 0.49 | 40.7 | 70.8 | 1.74 | 0.41 | 39.9 | 70.9 | 1.78 | 0.42 |
| 2 | 42.5 | 86.8 | 2.04 | 0.48 | 39.8 | 70.9 | 1.78 | 0.42 | 39.8 | 71.8 | 1.80 | 0.42 |
| 3 | 42.6 | 85.7 | 2.01 | 0.47 | 40.0 | 70.5 | 1.76 | 0.41 | 40.4 | 71.3 | 1.76 | 0.41 |
| 4 | 42.0 | 85.0 | 2.02 | 0.47 | 39.6 | 69.6 | 1.76 | 0.41 | 40.2 | 71.4 | 1.78 | 0.41 |
| 5 | 42.1 | 85.4 | 2.03 | 0.47 | 40.8 | 72.3 | 1.77 | 0.41 | 39.5 | 70.8 | 1.79 | 0.42 |
| MEAN | 42.10 | 85.74 | 2.04 | 0.48 | 40.18 | 70.82 | 1.76 | 0.41 | 39.96 | 71.24 | 1.78 | 0.42 |
| SD | 0.51 | 0.67 | 0.03 | 0.01 | 0.54 | 0.97 | 0.02 | 0.00 | 0.35 | 0.40 | 0.02 | 0.00 |
| CV | 1.22 | 0.78 | 1.24 | 1.24 | 1.34 | 1.37 | 0.90 | 0.90 | 0.88 | 0.57 | 0.86 | 0.86 |

The analysis of the inter-batch of reagents STA® Staclot® APC-R results grouped together in Table VII below also show good inter-batch of reagents overlapping.

The maximum deviation from one batch to another is less than 0.04 (absolute value) for the nSR-APC-R for the pathological control.

TABLE VII

| | STA STACLOT APCR 008 | | | | STA STACLOT APCR 009 | | | | STA STACLOT APCR 010 | | | |
|---|---|---|---|---|---|---|---|---|---|---|---|---|
| | −APC | +APC | APC-SR | n-APC-SR | −APC | +APC | APC-SR | n-APC-SR | −APC | +APC | APC-SR | n-APC-SR |
| Pool 5D6 002 | 46.5 | 180.9 | 3.89 | | 46.3 | 185.7 | 4.01 | | 42.2 | 168.0 | 3.98 | |
| | 45.9 | 179.6 | 3.91 | | 46.2 | 184.9 | 4.00 | | 42.1 | 167.8 | 3.99 | |
| CRT P: 7349A1D | 45.8 | 86.8 | 1.90 | 0.49 | 44.5 | 89.4 | 2.01 | 0.50 | 41.3 | 82.3 | 1.99 | 0.50 |
| | 47.1 | 87.1 | 1.85 | 0.47 | 44.5 | 88.3 | 1.98 | 0.50 | 42.1 | 83.0 | 1.97 | 0.49 |

TABLE VII-continued

| | STA STACLOT APCR 008 | | | | STA STACLOT APCR 009 | | | | STA STACLOT APCR 010 | | | |
|---|---|---|---|---|---|---|---|---|---|---|---|---|
| | −APC | +APC | APC-SR | n-APC-SR | −APC | +APC | APC-SR | n-APC-SR | −APC | +APC | APC-SR | n-APC-SR |
| CRT P: | 44.3 | 73.6 | 1.66 | 0.43 | 43.0 | 76.2 | 1.77 | 0.44 | 39.4 | 68.4 | 1.74 | 0.44 |
| 8005A2D | 44.4 | 74.9 | 1.69 | 0.43 | 42.4 | 74.0 | 1.75 | 0.44 | 39.7 | 70.4 | 1.77 | 0.45 |
| CRT P: | 44.5 | 75.9 | 1.71 | 0.44 | 43.4 | 74.6 | 1.72 | 0.43 | 39.7 | 70.3 | 1.77 | 0.44 |
| 8005B3D | 45.4 | 74.5 | 1.64 | 0.42 | 43.0 | 76.5 | 1.78 | 0.44 | 40.7 | 70.2 | 1.72 | 0.43 |

Example 7

Study of the Stability

1. Preservation:

A study of accelerated stability was carried out on the pathological control compositions at 30° C. for 3+2 weeks, in comparison with these same controls preserved at 2–8° C. The study of the results grouped together in Table VIII shows good preservation of the controls in lyophilized form (relative Δ of the times+APC over 3 weeks<5%).

25° C., stoppered bottles (study of 3 batches) place in an oven,
15–19° C. on STA, open bottles (study of 3 batches),
20° C., stoppered bottles.

All the determinations of the clotting times were carried out on STA in duplicate on the same batch of reagents (Staclot APC-R (010)) and relative to the same aliquoted pool. The analysis of the data grouped together in Tables IX, X, XI and XII makes it possible to propose as stability:

TABLE VIII

Preservation of the pathological controls APC-R for 3, 4, 5 weeks 8 at +30° C.

Staclot APC-R 010
Pool F 08/97
STA 502

| | Controls kept at 4° C. | | | | 3 weeks | | | | 4 weeks | | | | 5 weeks | | | |
|---|---|---|---|---|---|---|---|---|---|---|---|---|---|---|---|---|
| | −APC | +APC | APC-SR | n-APC-SR | −APC | +APC | APC-SR | n-APC-SR | −APC | +APC | APC-SR | n-APC-SR | −APC | +APC | APC-SR | n-APC-SR |
| 7349A1D | 41.5 | 80.6 | 1.94 | 0.48 | 42.0 | 79.8 | 1.90 | 0.47 | 42.0 | 80.4 | 1.91 | 0.47 | 41.8 | 82.0 | 1.96 | 0.48 |
| 8006A2D | 39.4 | 67.6 | 1.72 | 0.42 | 39.8 | 68.2 | 1.71 | 0.42 | 39.2 | 68.6 | 1.75 | 0.43 | 39.2 | 68.8 | 1.76 | 0.43 |
| 8006B3D | 40.2 | 69.4 | 1.73 | 0.42 | 39.7 | 69.2 | 1.74 | 0.43 | 39.9 | 69.9 | 1.75 | 0.43 | 39.7 | 70.8 | 1.78 | 0.44 |

| | Relative delta (T0/T3 wk.) | | | | Relative delta (T0/T4 wk.) | | | | Relative delta (T0/T5 wk.) | | | |
|---|---|---|---|---|---|---|---|---|---|---|---|---|
| | −APC | +APC | APC-SR | n-APC-SR | −APC | +APC | APC-SR | n-APC-SR | −APC | +APC | APC-SR | n-APC-SR |
| 7349A1D | 1.1 | −0.9 | −2.0 | −2.0 | 1.2 | −0.2 | −1.4 | −1.4 | 0.7 | 1.7 | 1.0 | 1.0 |
| 8006A2D | 1.1 | −1.0 | 0.2 | 0.2 | −0.4 | 1.5 | 1.9 | 1.9 | −0.5 | 1.9 | 2.4 | 2.4 |
| 8026B3D | 1.1 | −0.2 | 0.9 | 0.9 | −0.6 | 0.7 | 1.4 | 1.4 | −1.1 | 2.0 | 3.2 | 3.2 |

| | −APC | +APC | APC-SR |
|---|---|---|---|
| Pool 08/97 | 37.3 | 158.3 | 4.24 |
| | 40.2 | 157.2 | 3.91 |

2. Stability of the reagents:

The stability of the controls was studied after their first reconstitution at 4 temperatures:
2–8° C., stoppered bottles (study of 3 batches), stability in the apparatus: 8 h
stability at 2–8° C.: 8 h
stability at 25° C.: 6 h
stability at −20° C.: >24 h.

TABLE IX

Stability of the APCr P controls at 2–8° C. (closed bottles)

Staclot APCR 010

|  | T = 0 | | | | T = 4 hours | | | | T = 8 hours | | | | T = 12 hours | | | |
|---|---|---|---|---|---|---|---|---|---|---|---|---|---|---|---|---|
|  | −APC | +APC | APC-SR | n-APC-SR | −APC | +APC | APC-SR | n-APC-SR | −APC | +APC | APC-SR | n-APC-SR | −APC | +APC | APC-SR | n-APC-SR |
| Pool 08/97 | 39.6 | 163.3 | 4.12 | | | | | | | | | | | | | |
| 7349A1D | 40.1 | 82.3 | 2.05 | 0.50 | 41.0 | 84.6 | 2.06 | 0.50 | 41.0 | 84.4 | 2.06 | 0.50 | 42.5 | 86.7 | 2.94 | 0.50 |
| 8005B3D | 39.2 | 72.2 | 1.84 | 0.45 | 39.6 | 72.9 | 1.84 | 0.45 | 39.9 | 74.7 | 1.87 | 0.45 | 40.6 | 76.4 | 1.88 | 0.46 |
| 8026A4D | 37.5 | 64.0 | 1.71 | 0.41 | 37.6 | 64.8 | 1.72 | 0.42 | 38.9 | 65.5 | 1.69 | 0.41 | 38.7 | 66.9 | 1.73 | 0.42 |

|  | T = 20 hours | | | | T = 24 hours | | | | Relative delta % (T0/T8) | | | | Relative delta % (T0/12) | | | |
|---|---|---|---|---|---|---|---|---|---|---|---|---|---|---|---|---|
|  | −APC | +APC | APC-SR | n-APC-SR | −APC | +APC | APC-SR | n-APC-SR | −APC | +APC | APC-SR | n-APC-SR | −APC | +APC | APC-SR | n-APC-SR |
| 7349A1D | 42.5 | 89.4 | 2.10 | 0.51 | 43.3 | 89.6 | 2.07 | 0.50 | 2.2 | 2.6 | 0.4 | 0.4 | 6.1 | 5.4 | −0.7 | −0.7 |
| 8005B3D | 42.0 | 79.4 | 1.89 | 0.46 | 41.5 | 79.5 | 1.92 | 0.47 | 1.8 | 3.4 | 1.6 | 1.6 | 3.4 | 5.8 | 2.3 | 2.3 |
| 8026A4D | 39.7 | 70.1 | 1.77 | 0.43 | 40.8 | 72.8 | 1.78 | 0.43 | 3.6 | 2.3 | −1.2 | −1.2 | 3.1 | 4.5 | 1.3 | 1.3 |

TABLE X

Stability of the APCr P controls at 25° C. (closed bottles)

Staclot APCR 010

|  | T = 0 | | | | T = 2 hours | | | | T = 4 hours | | | |
|---|---|---|---|---|---|---|---|---|---|---|---|---|
|  | −APC | +APC | APC-SR | n-APC-SR | −APC | +APC | APC-SR | n-APC-SR | −APC | +APC | APC-SR | n-APC-SR |
| Pool 08/97 | 40.2 | 156.9 | 3.90 | | | | | | | | | |
| 7349A1D | 41.5 | 83.0 | 2.00 | 0.51 | 41.1 | 81.3 | 1.98 | 0.51 | 41.0 | 82.4 | 2.01 | 0.51 |
| 8005B3D | 38.8 | 69.5 | 1.79 | 0.46 | 39.1 | 70.9 | 1.81 | 0.46 | 39.2 | 70.5 | 1.80 | 0.46 |
| 8026A4D | 37.9 | 64.2 | 1.69 | 0.43 | 37.7 | 63.4 | 1.68 | 0.43 | 37.5 | 63.6 | 1.70 | 0.43 |

|  | T = 6 hours | | | | T = 8 hours | | | | Relative delta % (T0/T8) | | | |
|---|---|---|---|---|---|---|---|---|---|---|---|---|
|  | −APC | +APC | APC-SR | n-APC-SR | −APC | +APC | APC-SR | n-APC-SR | −APC | +APC | APC-SR | n-APC-SR |
| 7349A1D | 41.3 | 82;7 | 2.00 | | 41.4 | 83.1 | 2.01 | 0.51 | −0.2 | 0.1 | 0.4 | 0.4 |
| 8005B3D | 39.1 | 70.6 | 1.80 | | 39.9 | 71.0 | 1.78 | 0.46 | 2.8 | 2.2 | −0.6 | −0.6 |
| 8026A4D | 38.1 | 63.9 | 1.68 | | 37.8 | 63.5 | 1.68 | 0.43 | −0.3 | −1.0 | −0.8 | −0.8 |

TABLE XI

Stability of the APCr P controls on board (in the apparatus)

STA Staclot APCR 010

|  | T = 0 | | | | T = 2 hours | | | | T = 4 hours | | | | T = 6 hours | | | |
|---|---|---|---|---|---|---|---|---|---|---|---|---|---|---|---|---|
|  | −APC | +APC | APC-SR | n-APC-SR | −APC | +APC | APC-SR | n-APC-SR | −APC | +APC | APC-SR | n-APC-SR | −APC | +APC | APC-SR | n-APC-SR |
| Pool 08/97 | 39.1 | 158.5 | 4.05 | | | | | | | | | | | | | |
| 7349A1D | 41.8 | 82.1 | 1.97 | 0.49 | 42.7 | 84.4 | 1.98 | 0.49 | 42.0 | 83.1 | 1.98 | 0.49 | 42.3 | 82.1 | 1.94 | 0.48 |
| 8005B3D | 40.0 | 70.9 | 1.77 | 0.44 | 40.8 | 71.2 | 1.75 | 0.43 | 40.5 | 71.3 | 1.76 | 0.43 | 40.2 | 72.2 | 1.80 | 0.44 |
| 8026A4D | 37.1 | 62.9 | 1.69 | 0.42 | 37.8 | 64.2 | 1.70 | 0.42 | 37.8 | 64.8 | 1.72 | 0.42 | 38.1 | 63.6 | 1.67 | 0.41 |

TABLE XI-continued

Stability of the APCr P controls on board (in the apparatus)

| | T = 8 hours | | | | T = 10 hours | | | | Relative delta % (T0/T8) | | | | Relative delta % (T0/10) | | | |
|---|---|---|---|---|---|---|---|---|---|---|---|---|---|---|---|---|
| | −APC | +APC | APC-SR | n-APC-SR | −APC | +APC | APC-SR | n-APC-SR | −APC | +APC | APC-SR | n-APC-SR | −APC | +APC | APC-SR | n-APC-SR |
| 7349A1D | 41.6 | 82.1 | 1.99 | 0.49 | 42.1 | 83.7 | 1.99 | 0.49 | −0.4 | 0.7 | 1.0 | 1.0 | 0.7 | 1.9 | 1.2 | 1.2 |
| 8005B3D | 40.0 | 71.9 | 1.80 | 0.44 | 39.8 | 71.5 | 1.80 | 0.44 | 0.1 | 1.5 | 1.4 | 1.4 | −0.5 | 0.9 | 1.4 | 1.4 |
| 8026A4D | 37.8 | 64.4 | 1.71 | 0.42 | 37.9 | 64.3 | 1.70 | 0.42 | 1.8 | 2.5 | 0.7 | 0.7 | 2.0 | 2.2 | 0.2 | 0.2 |

TABLE XII

Stability of the APCr pathological controls at −20° C.

STA Staclot APCR 010

| | "Fresh" controls | | | | Controls kept 24 h at −20° C. | | | | Relative delta % | | | |
|---|---|---|---|---|---|---|---|---|---|---|---|---|
| | −APC | +APC | APC-SR | n-APC-SR | −APC | +APC | APC-SR | n-APC-SR | −APC | +APC | APC-SR | n-APC-SR |
| Pool 08/97 | 40.1 | 163.0 | 4.06 | | | | | | | | | |
| CRT P: 7349A1D | 41.1 | 81.3 | 1.98 | 0.49 | 41.3 | 83.4 | 2.02 | 0.50 | −0.5 | −2.6 | −2.1 | −2.1 |
| CRT P: 8005B3D | 39.8 | 71.2 | 1.79 | 0.44 | 39.4 | 71.1 | 1.81 | 0.44 | 1.1 | 0.1 | −1.0 | −1.0 |
| CRT P: 8026A4D | 38.0 | 62.2 | 1.69 | 0.42 | 37.8 | 63.4 | 1.68 | 0.41 | 0.5 | 1.3 | 0.8 | 0.8 |

Example 8

Example of a Kit Containing, as Pathological Control, Compositions According to the Invention Composition Each box contains 8 bottles (4 normal and 4 pathological) of lyophilized citrated plasma (1 ml after reconstitution).

Valuable Example

Each box of APC-R Normal and Pathological Controls contains a leaflet which has the following information: batch No., reference of the box, reference of the reagent, expiry date, value determined on STA® of clotting time for these reagents in the STA® Staclot® APC-R system.

These times may vary from one batch to another but are indicated precisely for each batch (see leaflet included in the box).

Preparation of the Reagent

Stir very precisely 1 ml of distilled water in each bottle. Stir vigorously. Allow the solution to stabilize for 1 hour at room temperature (18–25° C.). Stir gently to homogenize before use.

Stability of the Reagents

Lyophilization at 2–8° C. for a possible preservation up to the expiry date indicated on the box.

Reconstitution with distilled water knowing that the stability of the batches is the following 8 h on STA® (15–19° C.)

8 h at 2–8° C.

6 h at 25° C.

Instructions for Use

The control plasmas are used in the same manner as the plasmas to be tested.

REFERENCES

AMER L. et al., *Thromb. Res.*, 1990, 57, pages 247–258.

BERTINA R. M. et al., *Nature*, 1994, 369, pages 64–68.

DAHLBÄCK B. et al., *Thromb. Haemost.*, 1991, 65, abstract 39, page 658.

DAHLBÄCK B. et al., *Proc. Natl. Acad. Sci. USA*, 1993, 90, pages 1004–1008.

DAHLBÄCK et al., *Proc. Natl. Acad. Sci. USA*, 1994, 91, pages 1396–1400.

DE RONDE H. et al., *Thromb. Haemost.*, 1994, 72; pages 880–886.

KALAFATIS M. et al., *J. Biol. Chem.*, 1994, 269, pages 31869–31880.

KARGES H. E. et al., Arzneim.-Forsch./Drug Res., 44 (I), No. 6 (1994). P. 793–797).

LEWIS J. H.: *Comparative Hemostasis in vertebrates*, 1996, page 339.

MITCHELL C. A. et al., *N. Engl. J. Med.*, 1987, 317, pages 1638–1642.

SOULIER J. P. *NRFH*, 1975, volume 15, No. 2, pp 195–212.

SVENSSON P. J. et al., *N. Engl. J. Med.*, 1994, 330, pages 517–522.

VARADI K. et al., *Thromb. Haemost.*, 1995, 73, pages 730–731.

We claim:

1. A pathological control composition used in a method for the detection of resistance to activated protein C comprising normal plasma and animal serum rich in factor Va.

2. The composition as claimed in claim 1, wherein said normal plasma is human plasma.

3. The composition as claimed in claim 1, wherein said animal serum is bovine serum.

4. The composition as claimed in claim 1, wherein said serum does not contain vitamin K-dependent factors.

5. The composition as claimed in claim 1, wherein said serum does not contain factors II, VII, IX, X, PS, PC and PZ, or traces of fibrin.

6. The composition as claimed in claim 4, wherein said serum is obtained by absorbing a serum on barium sulfate and bentonite.

7. The composition as claimed in claim 1, wherein said animal serum contains a quantity of factor Va greater than 2000%.

8. The composition as claimed in claim 7, wherein said animal serum contains a quantity of factor Va greater than 2200%.

9. The composition as claimed in claim 1, wherein the proportion of said serum to said plasma is between 1/300 and 1/1200.

10. The composition as claimed in claim 9, wherein the proportion of said serum to said plasma is between 1/500 and 1/1000.

11. A method for preparing said composition as claimed in claim 1, comprising diluting an animal serum rich in factor Va in a normal plasma and selecting a dilution for which the clotting time in the presence of APC is situated in the interval defined for the clotting time in the presence of APC of an APC-R plasma, thereby obtaining the composition of claim 1.

12. The method as claimed in claim 11, wherein said normal plasma is human plasma.

13. The method as claimed in claim 11, wherein said animal serum is a bovine serum containing more than 2000% of factor Va.

14. The method as claimed in claim 13, wherein said bovine serum contains more than 2200% of factor Va.

15. The method as claimed in claim 11, wherein prior to diluting said serum is absorbed on barium sulfate and bentonite.

16. A method for the detection of resistance to APC comprising comparing the clotting time of a plasma to be tested with that of a composition as claimed in claim 1, and evaluating the level of APC resistance exhibited by said plasma.

17. The method as claimed in claim 16, which further comprises a chronometric method in which the results are expressed in the form of a normalized ratio, or as time or OD.

18. A kit for the diagnosis of resistance to activated protein C comprising as pathological control at least one composition as claimed in claim 1.

19. The composition as claimed in claim 2, wherein said normal plasma is citrated human plasma.

20. The method as claimed in claim 12, wherein said normal plasma is citrated human plasma.

* * * * *